United States Patent
Gambale

(10) Patent No.: US 6,942,665 B2
(45) Date of Patent: Sep. 13, 2005

(54) IMPLANTABLE DEVICE FOR COVERING AND OPENING IN A CRANIUM

(75) Inventor: Michael A. Gambale, Hingham, MA (US)

(73) Assignee: Integra Signature Technologies, Inc., Plainsboro, NJ (US)

( * ) Notice: Subject to any disclaimer, the term of this patent is extended or adjusted under 35 U.S.C. 154(b) by 664 days.

(21) Appl. No.: 10/136,132

(22) Filed: May 1, 2002

(65) Prior Publication Data

US 2003/0208205 A1 Nov. 6, 2003

(51) Int. Cl.⁷ ............................................. A61B 17/80
(52) U.S. Cl. ........................ 606/69; 606/73; 606/151
(58) Field of Search ............................. 606/61, 69, 70, 606/71, 151

(56) References Cited

U.S. PATENT DOCUMENTS

| 5,346,492 A | 9/1994 | Morgan |
| 5,814,048 A | 9/1998 | Morgan |
| 5,980,540 A | 11/1999 | Bruce |

*Primary Examiner*—David O. Reip
(74) *Attorney, Agent, or Firm*—Tarolli, Sundheim, Covell & Tummino L.L.P.

(57) ABSTRACT

An apparatus (10) for attachment to bone (18) comprises a plate (12) having a lower surface (28) for abutting against the bone (18) and an upper surface (30) opposite the lower surface (28). The plate (12) further includes a plurality of through-holes (32) extending between the lower and upper surfaces (28 and 30). Each through-hole (32) has an associated countersink (34). Each through-hole (32) defines a substantially square opening in the lower surface (28) of the plate (12) and each associated countersink (34) defines a circular opening in the upper surface (30) of the plate (12).

15 Claims, 2 Drawing Sheets

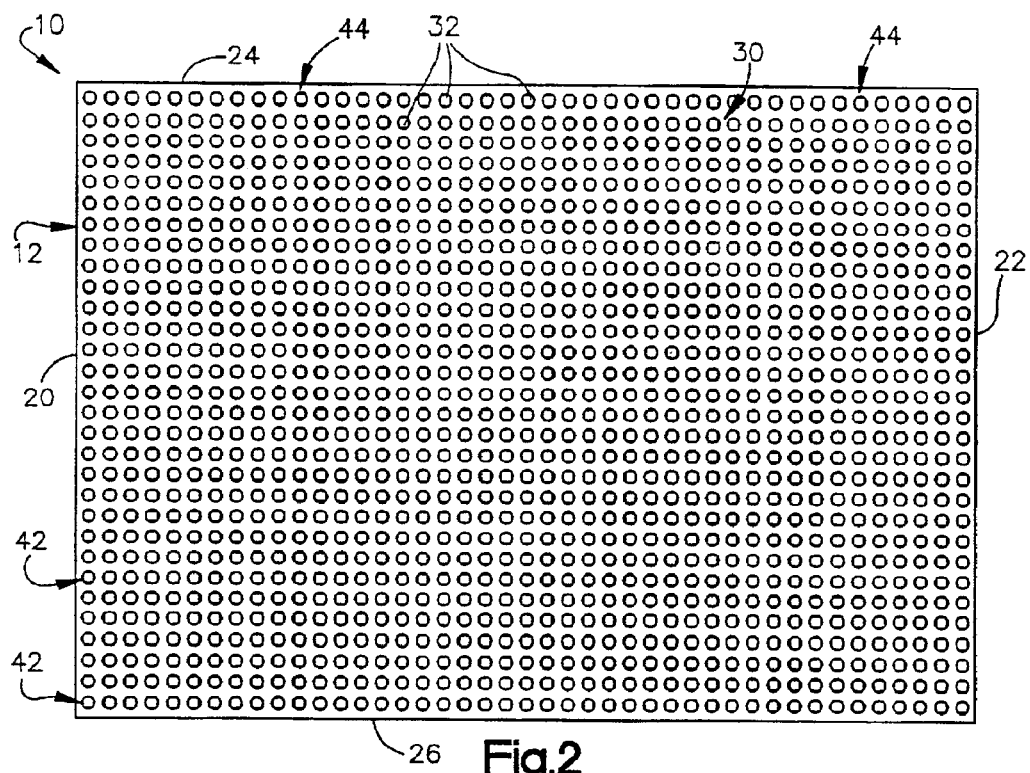
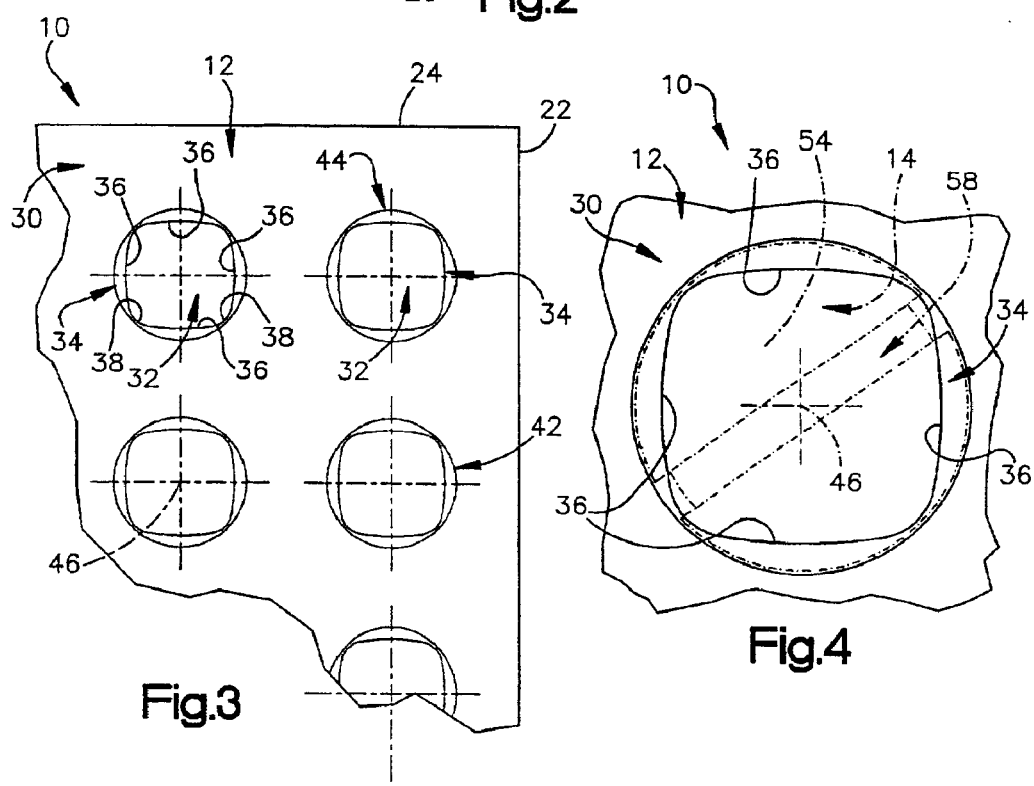

… (US 6,942,665 B2)

IMPLANTABLE DEVICE FOR COVERING AND OPENING IN A CRANIUM

TECHNICAL FIELD

The present invention relates to an implantable surgical mesh for attachment to bone. More particularly, the present invention relates to a cranial mesh for attachment to the cranium.

BACKGROUND OF THE INVENTION

A known surgical mesh for cranial applications is disclosed in U.S. Pat. No. 5,346,492. The known mesh includes a plurality of chamfered, square perforations, each for receiving a screw. The square configuration of the perforations makes the mesh more flexible than if the perforations were true circles. Clinical testing has shown that such a mesh having circular perforations is overly rigid and subject to cracking. By rounding the corners of generally square-shaped perforations, a mesh with sufficient flexibility and resistance to cracking is produced.

The square perforation design of the mesh in U.S. Pat. No. 5,346,492 has a drawback though. When a screw is received through a respective square perforation, only point contact is made between a head portion of the screw and each of the four surfaces defining the respective square perforation. Such point contact at four locations does not always provide sufficient attachment strength and may permit movement or shifting of the mesh. Consequently, a need exists for a mesh having perforations that provide for more than point contact with the bone screws, such as circular perforations, yet which retains adequate flexibility and resistance to cracking. Further, as with any cranial mesh, the mesh and bone screws should be as low profile (or thin in cross-section) as possible for aesthetic purposes.

SUMMARY OF THE INVENTION

The present invention relates to an apparatus for attachment to bone. The apparatus comprises a plate having a lower surface for abutting against the bone and an upper surface opposite the lower surface. The plate further includes a plurality of through-holes extending between the lower and upper surfaces. Each through-hole has an associated countersink. Each through-hole defines a substantially square opening in the lower surface of the plate and each associated countersink defines a circular opening in the upper surface of the plate.

According to another aspect, the present invention relates to an implantable device for covering an opening in a cranium. The device comprises a plate for covering the opening. The plate includes a peripheral portion for overlying a portion of the cranium surrounding the opening. The peripheral portion of the plate has a first plurality of through-holes that extends through the plate. Each through-hole of the first plurality of through-holes has a substantially square cross-sectional shape and includes a countersink located on a side of the plate opposite the cranium. The countersink has a circular cross-sectional shape. The device also comprises a plurality of bone screws. Each of the bone screws has a threaded shank portion and a head portion. The threaded shank portion of each of the bone screws is adapted to pass through an associated through-hole of the first plurality of through-holes and into the cranium. The head portion of each of the bone screws is adapted to make annular contact with the countersink of the associated through-hole for securing the plate relative to the cranium.

In accordance with yet another aspect, the present invention relates to a surgical mesh for covering an opening in a cranium. The surgical mesh comprises a malleable metal plate having a plurality of through-holes. Each through-hole has a substantially square cross-sectional shape and has an associated countersink with a circular cross-sectional shape.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 2 is a plan view of the apparatus of FIG. 1;

FIG. 3 is an enlarged plan view of a portion of FIG. 2;

FIG. 4 is a plan view illustrating a head portion of a bone screw received in the countersink of a respective through-hole of the apparatus of FIG. 1;

DETAILED DESCRIPTION OF THE INVENTION

Figure 1:
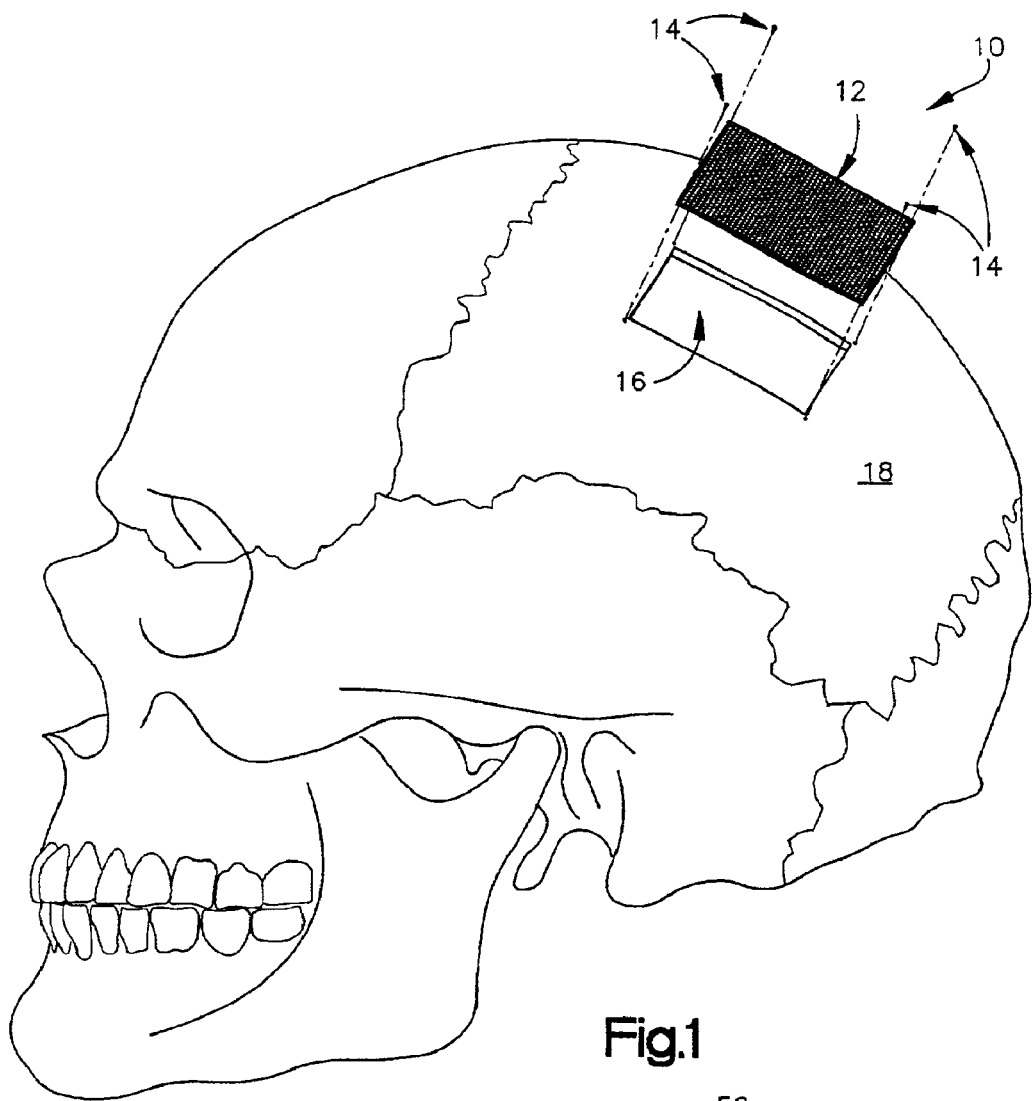
FIG. 1 is a perspective view illustrating an apparatus constructed in accordance with the present invention in spaced relation to an opening in a cranium.

An apparatus 10 constructed in accordance with the present invention is illustrated in FIG. 1. The apparatus 10 includes a cranial mesh. FIG. 1 illustrates the apparatus 10 in spaced relation to an opening 16 in a cranium 18. The cranial mesh 12 covers the opening 16 in the cranium 18 and is fixedly attached to the cranium with a plurality of bone screws 14, four of which are illustrated in FIG. 1.

FIG. 2 illustrates a plan view of the cranial mesh 12. In accordance with one embodiment of the invention, the cranial mesh 12 is a rectangular plate having first and second short side walls 20 and 22, respectively, and first and second long side walls 24 and 26, respectively. The distance between the first and second short side walls 20 and 22 defines a length of the cranial mesh 12 and the distance between the first and second long side walls 24 and 26 defines a width of the cranial mesh. The length and the width of the cranial mesh are chosen to completely cover the opening 16 in the cranium 18 and to overlay a portion of the cranium surrounding the opening.

The cranial mesh 12 includes a lower surface 28 (FIG. 5) and an upper surface 30. When fixedly attached to the cranium 18, a peripheral portion of the lower surface 28 abuts the cranium 18. The upper surface 30 is opposite the lower surface 28 and extends parallel to the lower surface.

The cranial mesh 12 is formed from a malleable, biocompatible, metallic material. In one embodiment, the cranial mesh 12 is formed from titanium. Prior to attachment of the cranial mesh 12 to the cranium 18, the cranial mesh 12 is shaped to correspond to the curvature of the cranium 18.

Figure 5:
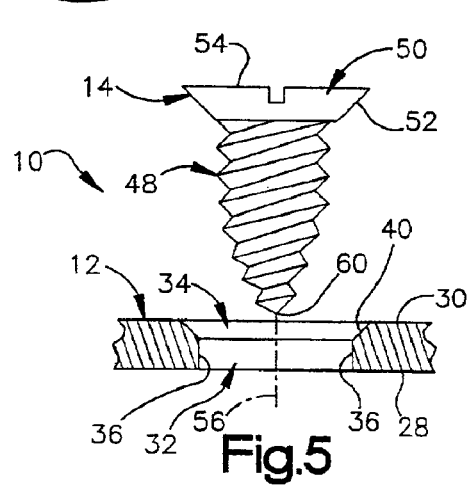
FIG. 5 illustrates a bone screw and a cross-section of a through-hole and an associated countersink of the apparatus of FIG. 1.

A plurality of through-holes 32 extends between the lower and upper surfaces 28 and 30 of the cranial mesh 12. Each through-hole 32 has an associated countersink 34 (FIGS. 3 and 5). The countersink 34 associated with each through-hole 32 is located adjacent the upper surface 30 of the cranial mesh 12. FIG. 5 illustrates a cross-sectional view of one of the through-holes 32 with its associated countersink 34. Each through-hole 32 of the plurality of through-holes has a generally square cross-sectional shape, as best shown in FIG. 3. Four through-hole side walls 36 define each through-hole 32. Rounded corners 38 (FIG. 3) connect adjacent through-hole side walls 36. Each through-hole 32 forms a generally square opening on a lower surface 28 of the cranial mesh 12. The square shape and the rounded corners 38 of the through-holes 32 provide the cranial mesh 12 with some flexibility and resistance to cracking.

Each countersink 34 has a depth of approximately one-third the distance between the upper and lower surfaces 28 and 30 of the cranial mesh 12. An annular tapered surface 40 (FIG. 5) defines the countersink 34 associated with each through-hole 32. The countersink 34 has a circular cross-sectional shape and forms a circular opening on the upper surface 30 of the cranial mesh 12. The diameter of the countersink 34 decreases as the annular tapered surface 40 extends away from the upper surface 30 of the cranial mesh 12 and toward the lower surface 28.

In the embodiment illustrated in FIG. 5, the annular tapered surface 40 extends at an angle of approximately 135 degrees relative to the upper surface 30 of the cranial mesh 12. The through-holes 32 and the associated countersinks 34 are machined into the cranial mesh 12.

As shown in FIG. 2, the plurality of through-holes 32 form an array of parallel extending rows 42 of through-holes and parallel extending columns 44 of through holes. In FIG. 2, each row 42 of through-holes 32 extends between the first and second short side walls 20 and 22 and each column 44 of through-holes extends between the first and second long side walls 24 and 26. As shown in FIG. 3, the distance between adjacent through-holes 32 in a respective column 44 is substantially equal to the distance between adjacent through-holes in a respective row 42.

Figure 6:
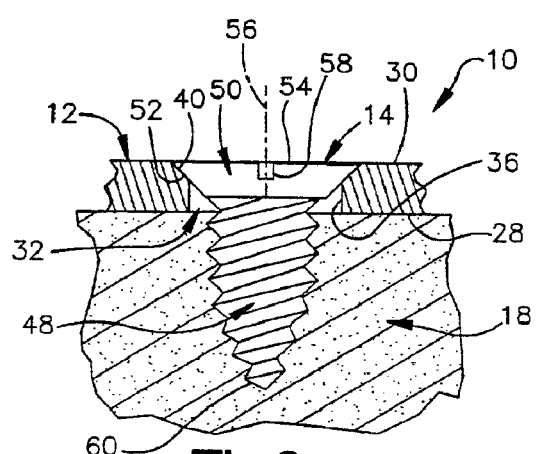
FIG. 6 illustrates a bone screw received in a through-hole of the apparatus of FIG. 1 and securing the apparatus to the cranium.

As shown in FIGS. 5 and 6, each bone screw 14 of the apparatus 10 includes a threaded shank portion 48 and a head portion 50. The threaded shank portion 48 has an axial length that is greater than the distance between the upper and lower surfaces 30 and 28 of the cranial mesh 12. The head portion 50 includes an annular tapered surface 52 and a generally flat upper surface 54. The annular tapered surface 52 of each bone screw 14 extends radially outwardly from the shank portion 48 at an angle of approximately 135 degrees relative to a central axis 56 of the bone screw. The upper surface 54 includes a slot 58 (FIG. 6) for receiving a driving tool (not shown).

Each through-hole 32 is adapted to receive the threaded shank portion 48 of a bone screw 14 and the countersink 34 associated with the through-hole is adapted to receive the head portion 50 of the bone screw. When a bone screw is received in a respective through-hole 32 and associated countersink 34, an end 60 of the threaded shank portion 48 of the bone screw 14 opposite the head portion 50 extends below the lower surface 28 of the cranial mesh 12 so that the threads of the threaded shank portion 48 may engage the bone of the cranium 18. When the head portion 50 of the bone screw 14 is received in the countersink 34, the annular tapered surface 52 of the head portion 50 of the bone screw 14 makes annular (or 360°) contact with the annular tapered surface 40 of the countersink 34. The annular contact between the head portion 50 of the bone screw 14 and the countersink 34 prevents movement of the cranial mesh 12 in all directions radial to the shank portion 48 of the bone screw 14 (i.e., radial to central axis 56). As may be seen in FIG. 6, the head portion 50 of the bone screw 14 is designed to seat fully within the countersink 34 so that the upper surface 54 of the head portion 50 lies flush with the upper surface 30 of the cranial mesh 12.

When covering an opening 16 in the cranium 18, a central portion of the cranial mesh 12 covers the opening 16 and a peripheral portion of the cranial mesh overlays a portion of the cranium 18 surrounding the opening. Preferably, the peripheral portion of the cranial mesh 12 includes two to three columns 44 of through-holes 32 adjacent each of the first and second short side walls 20 and 22 of the cranial mesh and two to three rows 42 of through-holes adjacent each of the first and second long side walls 24 and 26 of the cranial mesh. The peripheral portion of the cranial mesh 12 bounds the central portion of the cranial mesh. Bone screws 14 extend through through-holes 32 located in the peripheral portion of the cranial mesh 12 and into the portion of the cranium 18 surrounding the opening 16 to fixedly attach the cranial mesh to the cranium.

From the above description of the invention, those skilled in the art will perceive improvements, changes and modifications. For example, the shape of the cranial mesh 12 may be changed to correspond to the shape of the opening 16 in the cranium 18. Such improvements, changes and modifications within the skill of the art are intended to be covered by the appended claims.

Having described the invention, I claim the following:

1. An apparatus for attachment to bone, the apparatus comprising:
   a mesh-like plate having a lower surface for abutting against the bone and an upper surface opposite the lower surface;
   the plate further including a plurality of through-holes extending between the lower and upper surfaces, each through-hole having an associated countersink, each through-hole defining a substantially square opening in the lower surface of the plate and each associated countersink defining a circular opening in the upper surface of the plate.

2. The apparatus of claim 1 wherein each through-hole is adapted to receive a shank portion of a bone screw and wherein the associated countersink is adapted to receive a head portion of the bone screw.

3. The apparatus of claim 2 wherein the associated countersink of each through-hole is further adapted to make annular contact with the head portion of the bone screw when the head portion of the bone screw is received in the countersink.

4. The apparatus of claim 1 wherein the associated countersink of each through-hole is defined by an annular tapered surface, each associated countersink having a diameter that decreases as the annular tapered surface extends away from the upper surface of the plate toward the lower surface.

5. The apparatus of claim 4 wherein the annular tapered surface is angled relative to the upper surface of the plate at an angle of approximately 135 degrees.

6. The apparatus of claim 1 wherein the plurality of through-holes forms an array of parallel extending rows of through-holes and parallel extending columns of through-holes.

7. The apparatus of claim 6 wherein a distance between adjacent through-holes in a respective column of the array is substantially equal to a distance between adjacent through-holes in a respective row of the array.

8. The apparatus of claim 1 wherein the plate is formed from a biocompatible metallic material that is malleable into a shaped corresponding to a curvature of the bone.

9. The apparatus of claim 8 wherein the plate is formed from titanium.

10. An implantable device for covering an opening in a cranium, the device comprising:
a plate for covering the opening, the plate including a peripheral portion for overlying a portion of the cranium surrounding the opening, the peripheral portion of the plate having a first plurality of through-holes that extends through the plate, each through-hole of the first plurality of through-holes having a substantially square cross-sectional shape and including a countersink located on a side of the plate opposite the cranium, the countersink having a circular cross-sectional shape; and
a plurality of bone screws, each of the bone screws having a threaded shank portion and a head portion, the threaded shank portion of each of the bone screws being adapted to pass through an associated through-hole of the first plurality of through-holes and into the cranium, the head portion of each of the bone screws being adapted to make annular contact with the countersink of the associated through-hole for securing the plate relative to the cranium.

11. The device of claim 10 wherein the plate is malleable into a shape corresponding to a curvature of the portion of the cranium surrounding the opening.

12. The device of claim 10 wherein the head portion of each bone screw, when in annular contact with the countersink of an associated through-hole, prevents movement of the plate in all directions radial to the shank portion of the bone screw.

13. The device of claim 10 wherein the plate includes a central portion that is bounded by the peripheral portion, the central portion including a second plurality of through-holes that extends through the plate, the first and second plurality of through-holes collectively form an array of through-holes in the plate.

14. The device of claim 13 wherein each through-hole of the second plurality of through-holes includes an associated countersink located on a side of the plate opposite the cranium, each through-hole of the second plurality of through-holes having a substantially square cross-sectional shape and the associated countersink having a circular cross-sectional shape.

15. A surgical mesh for covering an opening in a cranium, the surgical mesh comprising:
a malleable metal plate having a plurality of through-holes, each through-hole having a substantially square cross-sectional shape and having an associated countersink with a circular cross-sectional shape.

* * * * *